United States Patent [19]

Metzger et al.

[11] Patent Number: 5,700,910
[45] Date of Patent: Dec. 23, 1997

[54] N-ACYL-S-(2-HYDROXYALKYL) CYSTEINES, THEIR PREPARATION AND THEIR USE AS INTERMEDIATES FOR THE PREPARATION OF SYNTHETIC IMMUNO-ADJUVANTS AND SYNTHETIC VACCINES

[75] Inventors: Jörg Metzger; Karl-Heinz Wiesmüller; Günther Jung, all of Tübingen, Germany

[73] Assignee: Hoechst Aktiengesellschaft, Frankfurt am Main, Germany

[21] Appl. No.: 475,437

[22] Filed: Jun. 7, 1995

Related U.S. Application Data

[63] Continuation of Ser. No. 116,549, Sep. 7, 1993, abandoned, which is a continuation of Ser. No. 898,719, Jun. 15, 1992, abandoned.

[30] Foreign Application Priority Data

Jun. 17, 1991 [DE] Germany ............ 41 19 856.5

[51] Int. Cl.$^6$ .................... C07K 1/02; C07C 321/00
[52] U.S. Cl. .................... 530/338; 530/333; 530/336; 530/345; 562/557
[58] Field of Search .................... 530/338, 333, 530/336, 345; 562/557

[56] References Cited

U.S. PATENT DOCUMENTS

| | | |
|---|---|---|
| 4,318,905 | 3/1982 | Nestor .................... 424/177 |
| 4,439,425 | 3/1984 | Tarcsay et al. .................... 424/177 |
| 4,666,886 | 5/1987 | Baschang et al. .................... 514/17 |
| 4,696,946 | 9/1987 | Green .................... 514/574 |
| 4,767,853 | 8/1988 | Hou .................... 540/357 |

FOREIGN PATENT DOCUMENTS

| | | |
|---|---|---|
| 0000330 | 8/1981 | European Pat. Off. |
| 3546150 | 1/1987 | Germany |

OTHER PUBLICATIONS

Kurimura et al. Chem. Pharm. Bull. 39(10) pp. 2590–2596 (Oct.' 91).
Metzger et al. Int. J. Pept. Prot. Res. 38 (1991) 545–554.
Jung et al. Liebigs Ann. Chem (1983) 1608–1622.
Tsuda et al. Chem. Pharm. Bull 39(3) 607–611 (Mar./1991).
Yuko Tsuda et al., "Structure and Synthesis of an Immunoactive Lipopeptide", Chem. Pharm. Bull. 39(3), pp. 607–611(1991).
Jorg W. Metzger et al., "Synthesis of $N_\alpha$-protected derivatives of S-(2,3-dihydroxypropyl)-cysteine and Their Application in Peptide Synthesis", Int. J. Peptide Protein Res. 38, 1991, pp. 545–554.
Gunther Jung et al., "The Mitogenic principle of *Escherichia coli* Lipoprotein: Synthesis, Spectroscopic Characterization, and Mitogenicity of N-Palmitoyl-S-[(2R,S)-2,3-dipalmitoyloxypropyl]-(R)-cysteine Methyl Ester", Liebigs Ann. Chem., 1983, pp. 1608–1622.
Petra Hoffman, et al., Biol. Chem. Hoppe–Seyler, vol. 370, pp. 575–582, 1989.
Karl–Heinz Wiesmuller, et al., Vaccine, vol. 7, pp. 29–33, 1989.
Karl–Heinz Wiesmuller, et al., Hoppe Seyler's Z. Physiol. Chem. vol. 364, pp. 593–606, 1983.
Lucas Lapatsanis et al., Synthesis, pp. 671–673, 1983.
Jorg Metzger et al., Int. J. Peptide Protein Res., vol. 37, pp. 46–57, 1991.

Primary Examiner—Cecilia J. Tsang
Assistant Examiner—David Lukton
Attorney, Agent, or Firm—Finnegan, Henderson, Farabow, Garrett & Dunner, L.L.P.

[57] ABSTRACT

N-Acyl-S-(2-hydroxyalkyl)cysteines, their preparation and their use as intermediates for the preparation of synthetic immunoadjuvants and synthetic vaccines.

Compounds of the formula I

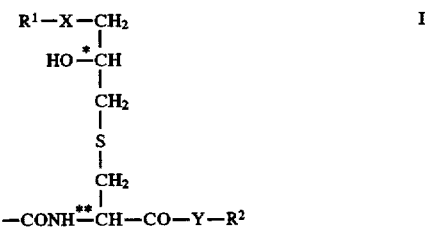

in which the substances X, Y, R, $R^1$ and $R^2$ have the meanings mentioned, are suitable for the preparation of lipopeptides and lipoamino acids.

2 Claims, No Drawings

N-ACYL-S-(2-HYDROXYALKYL) CYSTEINES, THEIR PREPARATION AND THEIR USE AS INTERMEDIATES FOR THE PREPARATION OF SYNTHETIC IMMUNO-ADJUVANTS AND SYNTHETIC VACCINES

This application is a continuation of prior application Ser. No. 08/116,549 filed Sep. 7, 1993, now abandoned, which is a continuation of application Ser. No. 07/898,719 filed Jun. 15, 1992, abandoned.

DESCRIPTION

The present invention relates to N-acyl-S-(2-hydroxyalkyl)cysteines, to a process for their preparation and to their use as intermediates for the preparation of synthetic immunoadjuvants and synthetic vaccines.

Some representatives of the class of compound mentioned have already been disclosed (EP 0,000,330). Using the known compounds, however, only a limited number of lipopeptides can be prepared.

Surprisingly, it has now been found that by means of novel N-acyl-S-(2-hydroxyalkyl)cysteines many lipopeptides can advantageously be prepared.

The invention accordingly relates to compounds of the formula I

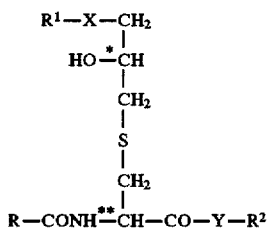

in which R is a fluorenylmethoxy, tert-butoxy or benzyloxy radical or a saturated or unsaturated, aliphatic or mixed aliphatic/cycloaliphatic hydrocarbon radical having 1 to 21 carbon atoms and optionally substituted by oxygen functions or halogen atoms, X is oxygen (O) or methylene ($CH_2$), Y is oxygen or an amino acid radical optionally side-chain-protected by a protective group customary in peptide chemistry, $R^1$ is hydrogen, a saturated or unsaturated, aliphatic or mixed aliphatic/cycloaliphatic hydrocarbon radical having 1 to 21 carbon atoms and optionally substituted by oxygen functions or halogen atoms, or a radical of the formula C(O)—$R^3$, where $R^3$ is a saturated or unsaturated, aliphatic or mixed aliphatic/cycloaliphatic hydrocarbon radical having 1 to 21 carbon atoms and optionally substituted by oxygen functions or halogen atoms, and $R^2$ is tert-butyl, methyl, ethyl, propyl or benzyl, where the compounds are excluded in which R is a hydrocarbon radical, $R_1$=H, X=O, Y=O and $R_2$=tert-butyl (disclosed in EP 0,000, 330). The compounds have the absolute R- or S-configuration at the centers of asymmetry designated by * or ** and exist as pure diastereomers or optionally as diastereomer mixtures.

Preferred compounds of the formula I are those in which R is a fluorenylmethoxy, tert-butoxy or a saturated aliphatic hydrocarbon radical having 5 to 17 carbon atoms, X is oxygen or methylene ($CH_2$) and Y is oxygen, $R^1$ is hydrogen, a saturated aliphatic hydrocarbon radical having 7 to 18 carbon atoms or a radical of the formula C(O)—$R^3$, where $R^3$ is a saturated hydrocarbon radical having 5 to 17 carbon atoms, and $R^2$ is tert-butyl. Preferred compounds are furthermore those which have the absolute R-configuration at the centers of asymmetry designated by * or **.

Very particularly preferred compounds of the formula I are those in which R is a fluorenylmethoxy or a saturated aliphatic hydrocarbon radical having 11 to 17 carbon atoms, X is oxygen and Y is oxygen, $R^1$ is hydrogen, a saturated aliphatic hydrocarbon radical having 9 to 18 carbon atoms or a radical of the formula C(O)-$R^3$, where $R^3$ is a saturated hydrocarbon radical having 9 to 17 carbon atoms, and $R^2$ is tert-butyl. Very particularly preferred compounds are those which have the absolute R-configuration at the centers of asymmetry designated by * or **.

The abovementioned hydrocarbon radicals can be up to trisubstituted by oxygen functions and/or by halogen atoms. The hydrocarbon radicals can be mono- or poly-unsaturated, preferably they are up to triunsaturated.

The side-chain-protected amino acids, preferably natural amino acids, can be provided with protective groups customary in peptide chemistry. Those preferred are tert-butyl, tert-butoxycarbonyl, 4-methoxy-2,3,6-trimethyl-benzenesulfonyl, 9-fluorenylmethoxycarbonyl, in particular tert-butyl and tert-butoxycarbonyl.

The compounds described are particularly suitable as intermediates for the preparation of synthetic adjuvants (EP 0,000,330; U.S. Pat. No. 4,666,886, B lymphocytes and macrophage stimulants (P. Hoffmann, K.-H. Wiesmüller, J. Metzger, G. Jung, W. G. Bessler, Biol. Chem. Hoppe-Seyler 370 (1989) 575) and synthetic vaccines; Wiesmüller K.-H., Jung, G. Hess, G. vaccines 7 (1989) 29, DE-A-3,546,150).

The present invention furthermore relates to a process for the preparation of compounds of the abovementioned formula I, which comprises reducing a compound of the formula II

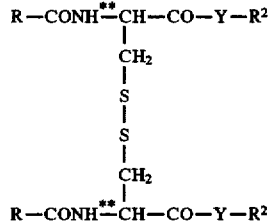

with Zn in an $HCl/H_2SO_4$/solvent mixture and reacting with a compound of the formula III

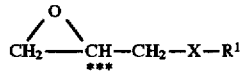

to give a compound of the formula I, where R, $R^1$, $R^2$, X and Y have the abovementioned meanings. The epoxides of the formula III have the R or S absolute configuration at the center of asymmetry marked by ***, and are in enantiomerically pure form or optionally as a racemate.

The process according to the invention is particularly suitable for the preparation of the above compounds of the formula I described as preferred, in particular for the preparation of the compounds mentioned where $R^1$=H and X=O.

It has surprisingly been found that bis-N-acylated cystine diesters can be reduced under the conditions mentioned according to the invention in a "one-pot reaction" using zinc and acid and can be alkylated with epoxides in high yield without prior isolation of the resulting cysteine derivatives even if acid-labile protective groups such as, for example, tert-butyl esters are present. The reaction can be carried out in several steps, but preferably takes place as a one-pot reaction. The advantages of the reaction described consist, inter alia, in that no isolation of the reduction products is necessary, in that it proceeds under mild conditions to give high yields of diastereomerically pure products and in that the working up of the reaction mixture is very simple.

For example, K.-H. Wiesmüer, W. Bessler, G. Jung, Hoppe Seyler's Z. Physiol. Chem. 364 (1983) 593 describe the preparation of the starting substances of the formula II.

Starting substances of the formula II in which R is a fluorenylmethoxy, tert-butoxy or benzyloxy radical can be obtained in a known manner, for example, by reaction of the corresponding cystine bis ester with fluorenyl-methoxycarbonyl-M-hydroxysuccinimide ester (Lapatsanis, L., Milias, G., Froussios, K., Kolovos, M. (1983) Synthesis, 671–673).

The compounds of the formula III are commercially available as a racemate and in enantiomerically pure form (for example Aldrich, Fluka, Merck).

The following solvents are preferably used for the Zn/HCl (for example 32%, d=1.16)/H$_2$SO$_4$ (d=1.84)/solvent mixture: methanol, ethanol, n-propanol, 2-propanol and n-butanol, very particularly preferably methanol, ethanol and 2-propanol, in particular methanol.

The volume ratio of the two acid components HCl (32%, d=1.16) and H$_2$SO$_4$ (d=1.84) is preferably in the range 10:1 to 2:1, very particularly preferably 10:1 to 5:1, in particular 7:1. The volume ratio acid components/solvent is expediently in the range 1:100 to 10:100, preferably 1:100 to 5:100, in particular 4:100.

The ratio of the equivalents of zinc to the compound of the formula II is expediently 5:1 to 20:1, preferably 5:1 to 10:1, very particularly preferably 5:1 to 8:1.

The ratio of the equivalents of compound of the formula II to the compound of the formula III is expediently 1:2 to 1:40, preferably 1:4 to 1:20, very particularly preferably 1:10.

The reaction temperature is preferably in the range 20°–70° C.

The reduction of the compound of the formula II with Zn and in situ alkylation with a compound of the formula III is preferably carried out under the following conditions: the ratio of the equivalents of zinc to the compound of the formula II is 7:1, the volume ratio of the two acid components HCl (32%, d=1.16) and H$_2$SO$_4$ (d=1.84) is 7:1. The volume ratio acid components/solvent is preferably about 4:100. Methanol is preferably used as the solvent. The ratio of the equivalents of the compound of the formula II to the compound of the formula III is preferably 1:10. The preferred reaction temperature is about 45° C.

The compound of the formula I is then isolated by filtering and the filtrate is concentrated on a rotary evaporator. More lipophilic compounds precipitate on pouring the concentrated filtrate into water and can be isolated very easily by filtration. Less lipophilic compounds and compounds which are obtained as an oil are purified by rapid flash chromatography on silica gel using chloroform as the eluent.

The N-acyl-S-(2-hydroxyalkyl) cysteines obtained are intermediates in the preparation of lipopeptides which are used as synthetic immunoadjuvants and synthetic vaccines and as stimulants of B lymphocytes and macrophages.

The process is particularly suitable for the preparation of intermediates in the synthesis of the lipoamino acid S-[2,3-bis(palmitoyloxy)propyl]cysteine (Pam$_3$Cys-OH; K.-H. Wiesmüller, W. Bessler, G. Jung, Hoppe Seyler's Z. Physiol. Chem. 364 (1983) 593) and of lipopeptides which contain this lipoamino acid or an analog thereof at the N terminus. The latter have considerable importance in the development of synthetic immunoadjuvants and synthetic vaccines.

The possibility exists of removing C-terminal protective groups in the compounds of the formula I (Y=oxygen, X, R, $R^1$ and $R^2$ as above) using processes of peptide chemistry known per se (for example treatment with trifluoroacetic acid to remove tert-butyl or treatment with NaOH to hydrolyze methyl esters), and using the compounds of the formula I thus obtained ($R^2$=hydrogen, Y=oxygen, and X, R, $R^1$ as above) for the synthesis of lipopeptides, preferably in solid phase peptide syntheses. Solid phase peptide syntheses have been known for a long time. Likewise, the amino acids or peptides to be used for the preparation according to the process for the synthesis of the peptide chain of the novel lipopeptides are known or can be prepared by methods known per se.

The free hydroxyl group (s) of the resin-bonded N-acyl-S-( 2-hydroxyalkyl ) cysteinyl peptide can be esterified directly on the resin with acids. For this purpose, acid chlorides of the formula IV

are preferably used where $R^4$ is a preferably saturated but also unsaturated, aliphatic or mixed aliphatic/cycloaliphatic hydrocarbon radical having 1 to 21 carbon atoms, preferably having 11 to 19 and very particularly preferably having 11 to 17 carbon atoms, and optionally substituted by oxygen functions or halogen atoms. The solvent for this acylation is very particularly preferably pyridine/dichloromethane. (1:1; v:v).

When using compounds of the formula I where R=fluorenylmethoxy, Y=oxygen, $R^3$=hydrogen and X, R and $R^1$ are as described above, the possibility exists after coupling to a resin-bonded peptide of removing the base-labile amino-protective group on the N terminus fluorenyl-methoxycarbonyl using methods known per se (for example treatment with piperidine/DMF 1:1). The N terminus of the resin-bonded peptide can be lengthened under customary coupling conditions with suitable other amino acid derivatives or aminated in pyridine/dicholoromethane (1:1, v:v) with acid chlorides of the formula IV, where $R^4$ has the abovementioned meaning.

The crucial advantage of carrying out the N- and O-acylation in two separate steps is the possibility of synthesizing lipopeptides in a simple manner which differ in the nature of their ester- and amide-like bonded fatty acids.

The removal of the resin-bonded lipopeptides is carried out in a manner known per se, for example when using acid-labile anchor groups with trifluoroacetic acid (see, for example, Metzger, J., Wiesmüll er, K.-H., Schaude, R., Bessler, W. G und Jung, G. (1991): Synthesis of Novel Immunologically Active Tripalmitoyl-S-glycerylcysteinyl Lipopeptides as Useful Intermediates for Immunogen Preparations, Int. J. Peptide Prot. Res. 37, 46–57 (1991)).

The following exemplary compounds can be obtained by the abovementioned preparation process according to the invention:

N$_a$-Fluorenylmethoxycarbonyl-S-[2,3-dihydroxy-[2R]-propyl]-[R]-cysteine tert-butyl ester N$_a$-Fluorenylmethoxycarbonyl-S-[2,3-dihydroxy-[2S]-propyl]-[R]-cysteine tert-butyl ester N$_a$-Fluorenylmethoxycarbonyl-S-[2,3-dihydroxy-[2R,S]-propyl]-[R]-cysteine tert-butyl ester N-Palmitoyl-S-(2[R,S]-hydroxy)octadecylcysteine tert-butyl ester N-Palmitoyl-S-[2-hydroxy-3-palmitoyloxy[2R,S]-propyl] cysteine tert-butyl ester N-Palmitoyl-S-[2-hydroxy-3-hexadecyloxy[2R,S]-propyl] cysteine tert-butyl ester N-palmitoyl-S-[2-hydroxy-3-butoxy[2R,S]-propyl]cysteine tert-butyl ester N-palmitoyl-S-[2-hydroxy-3-methoxy[2R,S]-propyl] cysteine tert-butyl ester The hydroxyl functions of the abovementioned compounds can be acylated to give the following compounds using appropriate acid chlorides either in solution or in resin-bonded form on the resin in mixtures of pyridine and dichloromethane (1:1, v:v):

$N_a$-Fluorenylmethoxycarbonyl-S-[2,3-bis(palmitoyloxy)-[2R]-propyl]-[R]-cysteine tert-butyl ester $N_a$-Fluorenylmethoxycarbonyl-S-[2,3-bis(palmitoyloxy)-[2S]-propyl]-[R]-cysteine tert-butyl ester $N_a$-Fluorenylmethoxycarbonyl-S-[2,3-bis(palmitoyloxy)-[2R,S]-propyl]-[R]-cysteine tert-butyl ester N-palmitoyl-S-(2[R,S]-palmitoyloxy)octadecylcysteine tert-butyl ester N-palmitoyl-S-[2,lauroyloxy-3-palmitoyloxy-[2R,S]-propyl]cysteine tert-butyl ester N-palmitoyl-S-[2-lauroyloxy-3-hexadecyloxy[2R,S]-propyl]cysteine tert-butyl ester N-palmitoyl-S-[2-stearoyloxy-3-butyloxy[2R,S]-propyl] cysteine tert-butyl ester N-palmitoyl-S-[2-stearoyloxy-3-methoxy[2R,S]-propyl] cysteine tert-butyl ester From the corresponding abovementioned tert-butyl esters, the following important amino acid derivatives can be obtained by treatment with pure trifluoroacetic acid:

$N_a$-Fluorenylmethoxycarbonyl-S-[2,3-dihydroxy-[2R]-propyl]-[R]-cysteine $N_a$-Fluorenylmethoxycarbonyl-S-[2,3-dihydroxy-[2S]-propyl]-[R]-cysteine $N_a$-Fluorenylmethoxycarbonyl-S-[2,3-dihydroxy-[2R,S]-propyl]-[R,R]-cysteine $N_a$-Fluorenylmethoxycarbonyl-S-[2,3-bis(palmitoyloxy)-[2R]-propyl]-[R]-cysteine $N_a$-Fluorenylmethoxycarbonyl-S-[2,3-bis(palmitoyloxy)-[2S]-propyl]-[R]-cysteine $N_a$-Fluorenylmethoxycarbonyl-S-[2,3-bis(palmitoyloxy)-[2R,S]-propyl]-[R]-cysteine N-palmitoyl-S-(2[R,S]-hydroxy)octadecylcysteine N-palmitoyl-S-(2[R,S]-palmitoyloxy)octadecylcysteine N-palmitoyl-S-[2-hydroxy-3-palmitoyloxy[2R,S]-propyl] cysteine N-palmitoyl-S-[2-hydroxy-3-hexadecyloxy[2R,S]-propyl] cysteine N-palmitoyl-S-[2-hydroxy-3-butyloxy[2R,S]-propyl] cysteine N-palmitoyl-S-[2-hydroxy-3-methoxy[2R,S]-propyl] cysteine N-palmitoyl-S-[2-lauroyloxy-3-palmitoyloxy[2R,S]-propyl]cysteine N-palmitoyl-S-[2-lauroyloxy-3-hexadecyloxy[2R,S]-propyl]cysteine N-palmitoyl-S-[2-stearoyloxy-3-butyloxy[2R,S]-propyl] cysteine N-palmitoyl-S-[2-stearoyloxy-3-methoxy[2R,S]-propyl] cysteine The present invention, which is also characterized by the contents of the patent claims, is intended to be illustrated in greater detail by the following exemplary embodiments:

All example compounds mentioned below were examined by ion spray mass spectrometry IS-MS and IS-MS/MS. The compounds could be characterized clearly both by means of their molecular weight and by means of their fragmentation.

In TLC, silica gel is used as an adsorbent and the following systems as eluents:

I, chloroform/methanol/water (65:25:4); II, chloroform/methanol/glacial acetic acid (90:10:1); III, ethyl acetate saturated with water; IV, 1-butanol/glacial acetic acid/water (2:1:1); V, chloroform/methanol (8:2); VI, chloroform/methanol/17% ammonia (2:2:1). VII, chloroform. For detection, plates were sprayed with water, ninhydrin reagent and chlorine/4,4'-bis(dimethylamino)diphenylmethane (TDM reagent).

Example 1
$N_a$-Fluorenylmethoxycarbonyl-S-[2,3-dihydroxy-propyl]-[$R_1$-cysteine tert-butyl ester Zinc (1.1 g; 16.8 mmol) and a freshly prepared solution of methanol, 32% hydrochloric acid (d=1.16) and concentrated sulfuric acid (d=1.84) (100:7:1; 8 ml) were added with vigorous stirring to a solution of N,N'-dipalmitoylcystine di-tert-butyl ester (1.92 g; 2.4 mmol) in dichloromethane (15 ml). After 15 min, (S)-(−)-glycidol (1.78 g=1.6 ml; 2.4 mmol) was added. The mixture was stirred at 40° C. for 5 h. The solvent was concentrated to about half the original volume and diluted with 5% KHSO$_4$ (2 ml). This mixture was kept at −4° C. for 16 h and extracted 3 times by shaking with dichloromethane. The organic phase was dried over Na$_2$SO$_4$ and concentrated to dryness. The ester was obtained as a colorless oil. Yield for the RR-diastereomer: 2.06 g (91%). $R_f$(I)=0.72; $R_f$(II)=0.47; $R_f$(IV)=0.45; C$_{25}$H$_{31}$N O$_6$S (473.6). Analogously, using (R)-(+)-glycidol the RS-diastereomer (yield 1.93 g; 85%) and using racemic glycidol the mixture R(R/S) of both diastereomers were obtained. $^{13}$C-NMR: see following table.

Allocation of the $^{13}$C-NMR signals for $N_a$-fluorenylmethoxycarbonyl-S-[2,3-dihydroxy-propyl] cysteine tert-butyl ester
(CDCl$_3$; 200 mg/ml; 20,115 MHz):

|  | RR | RS | R(R/S) |
| --- | --- | --- | --- |
| t-Bu—CH$_3$ | 27.9 | 27.9 | 27.9 |
| S-glyceryl CH$_2$ | 35.5 | 35.4 | 35.4/35.5 |
| Cys-C$_B$ | 36.2 | 36.3 | 36.2/36.3 |
| Fmoc-C-9 | 47.1 | 47.0 | 47.0 |
| Cys-C$_\alpha$ | 54.6 | 54.5 | 54.5 |
| S-glyceryl CH$_2$—OH | 65.1 | 65.1 | 65.0/65.0 |
| Fmoc-CH$_2$—O | 67.2 | 67.2 | 67.1 |
| S-glyceryl CH—OH | 71.0 | 71.1 | 71.0/71.0 |
| TbU-C$_q$ | 83.0 | 82.9 | 82.9 |
| Fmoc-C-4,5 | 120.0 | 119.9 | 119.9 |
| Fmoc-C-1,8 | 125.1 | 125.1 | 125.1 |
| Fmoc-C-3,2,6,7 | 127.1 | 127.1 | 127.0 |
| Fmoc-C-3,2,6,7 | 127.7 | 127.7 | 127.7 |
| Fmoc-C-4a,4b | 141.2 | 141.2 | 141.2 |
| Fmoc-C-8a,9a | 143.7 | 143.7 | 143.7 |
| Fmoc-CO | 156.2 | 156.1 | 156.1 |
| Cys-CO | 169.9 | 169.9 | 169.3 |

The N,N'-bis(fluorenylmethoxycarbonyl)-[R]-cystine di-tert-butyl ester used in the preliminary step was prepared by the following procedure: L-cystine di-tert-butyl ester (3.52 g; 10 mmol) and fluorenylmethoxycarbonyl-N-hydroxysuccinimide ester (5.4 g; 16 mmol) were dissolved in tetrahydrofuran (10 ml). A solution of N-ethylmorpholine (2.55 g; 20 mmol) in tetrahydrofuran (5 ml) was added. After 3 h, the mixture was concentrated to dryness. The residue was dissolved in ethyl acetate and washed 3 times with 5% KHSO$_4$ and water. The organic phase was dried over Na$_2$SO$_4$ and concentrated to dryness. The residue was recrystallized from dichloromethane/methanol (1:4; 300 ml) at −20° C. The precipitate was washed twice with tert-butanol/2-propanol (1:1) and dried over P$_4$O$_{10}$/KOH. Yield: 6.9 g (87%). $R_f$(II)=0.89; $R_f$(III)=0.81; $R_f$(IV)=0.80; $R_f$(V)=0.21. C$_{44}$H$_{48}$N$_2$O$_8$S$_2$ (797.0). Ion spray MS [M+H]$^+$ 798. $^{13}$C-NMR (CDCl$_3$; 150 mg/ml; 120 scans; 20.115 MHz): δ (ppm)=27.9 (3x tBu-CH$_3$); 41.8 (Cys-C$_B$); 47.0

(Fmoc-C-9); 54.1 (Cys-C$_\alpha$); 67.2 (Fmoc-CH$_2$-O); 83.0 (Cys-OtBu-C$_q$); 119.9 (Fmoc-C-4,5); 125.1 (Fmoc-C-1,8); 127.6, 127.0 (Fmoc-C-3,2,6,7); 141.2 (Fmoc-C-4a,4b); 143.8, 143.7 (Fmoc-C-8a,9a); 155.7 (Fmoc-CO); 169.3 (Cys-CO).

The L-cystine di-tert-butyl ester used in the preliminary step was prepared by a known literature procedure (K.-H. Wiesmüller, W. Bessler, G. Jung, Hoppe Seyler's Z. Physiol. Chem. 364 (1983) 593).

Example 2

N-Palmitoyl-S-(2-[R,S]-hydroxy)octadecylcysteine tert-butyl ester

N,N'-Dipalmitoylcystine di-tert-butyl ester (2 g; 2.42 mmol) were dissolved in methanol (15 ml) with slight warming and treated with zinc dust (1.1 g; 16.8 mmol). A mixture (7:1; 1 ml) of conc. HCl (32%, d=1.16) and conc. sulfuric acid (d=1.84) was added dropwise with vigorous stirring via a dropping funnel. After 15 min, 1,2-epoxyoctadecane (1.3 g; 4.84 mmol) was added. The mixture was stirred at 45° C. for 10 h. After completion of the reaction, the solvent was removed on a rotary evaporator and the product was precipitated from chloroform at –20° C. For further purification, it was chromatographed on silica gel (column 80×2.5 cm; eluent: chloroform). The product fractions were combined and obtained in high purity as a colorless powder by a further precipitation from methanol at 4° C. Yield: 2.4 g (73%). C$_{41}$H$_{81}$NO$_4$S 684.2; ion spray MS and MS/MS: see FIG. 1. (R$_f$(VII)=0.41.

Example 3

N-Palmitoyl-S-[2-hydroxy-3-palmitoyloxy-[2R,S]-propyl]cysteine tert-butyl ester

N,N'-Dipalmitoylcystine di-tert-butyl ester (1 g; 1.21 mmol) was dissolved in methanol (10 ml) with slight warming and treated with zinc dust (550 mg; 8.5 mmol). A mixture (7:1; 0.5 ml) of conc. HCl (32%, d=1.16) and conc. sulfuric acid (d=1.84) was added dropwise with vigorous stirring via a dropping funnel. After 20 min, 2,3-epoxypropyl palmitoate (1.62 g; 4.84mmol) was added. The mixture was stirred at 45° C. for 10 h. After completion of the reaction, the solvent was removed on a rotary evaporator and the product was precipitated from methanol/glacial acetic acid/water (5:1:1) at –20° C. and lyophilized from tert-butanol. A further precipitation from methanol at 4° C. yielded the lipoamino acid ester in high purity. Yield: 1.25 g (71%). C$_{42}$H$_{81}$NO$_6$S 728.2; ion spray MS: [M+H]+729; R$_f$(VI)=0.34.

The N,N'-dipalmitoylcystine di-tert-butyl ester used above was prepared according to a literature procedure (K.-H. Wiesmüller, W. Bessler, G. Jung, Hoppe Seyler's Z. Physiol. Chem. 364 (1983) 593); this also applies to 2,3-epoxypropyl palmitoate (Kester et al., J. Org. Chem. 8, 553, 1943).

Example 4

N-Palmitoyl-S-[2-hydroxy-3-butyloxy-[2R,S]-propyl]cysteine tert-butyl ester

N,N'-Dipalmitoylcystine di-tert-butyl ester (1 g; 1.21 mmol) was dissolved in methanol (10 ml) with slight warming and treated with zinc dust (280 mg; 4.3 mmol). A mixture (7:1; 0.5 ml) of conc. HCl (32%, d=1.16) and conc. sulfuric acid (d=1.84) was added dropwise with vigorous stirring via a dropping funnel. After 10 min, glycidyl butyl ether (0.63 g; 4.84 mmol) was added. The mixture was stirred at 45° C. for 5 h. After completion of the reaction, the solvent was removed on a rotary evaporator. For purification, the residue was chromatographed on silica gel (column 80×2.5 cm; eluent: chloroform). The product fractions were combined and concentrated to dryness and the resulting colorless oil was dried in a high vacuum. Yield: 0.95 g (72%). C$_{30}$H$_{59}$NO$_5$ 545.9; ion spray MS: [M+H]$^+$ 547; R$_f$(III)=0.34.

The N,N'-dipalmitoylcystine di-tert-butyl ester used above was prepared by a literature procedure (K.-H. Wiesmüller, W. Bessler, G. Jung, Hoppe Seyler's Z. Physiol. Chem. 364 (1983) 593).

We claim:

1. A process for the preparation of a compound of formula I

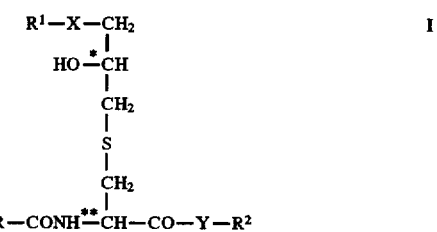

in which R is a fluorenylmethoxy, tert-butoxy or benzyl-oxy radical or a saturated or unsaturated, aliphatic or mixed aliphatic/cycloaliphatic hydrocarbon radical having 1 to 21 carbon atoms and optionally substituted by oxo groups or halogen atoms, X is oxygen or methylene, Y is oxygen or an amino acid radical optionally side-chain-protected by a protective group, R$^1$ is hydrogen, a saturated or unsaturated, aliphatic or mixed aliphatic/cycloaliphatic hydrocarbon radical having 1 to 21 carbon atoms and optionally substituted by oxo groups or halogen atoms, or a radical of the formula, C(O)—R$^3$ where R$^3$ is a saturated or unsaturated, aliphatic or mixed aliphatic/cycloaliphatic hydrocarbon radical having 1 to 21 carbon atoms and optionally substituted by oxo groups or halogen atoms, and R$^2$ is tert-butyl, methyl, ethyl, propyl or benzyl, where the compounds are excluded in which R is a hydrocarbon radical, R$_1$=H, X=O, Y=O and R$_2$=tert-butyl; which comprises reducing a compound of formula II

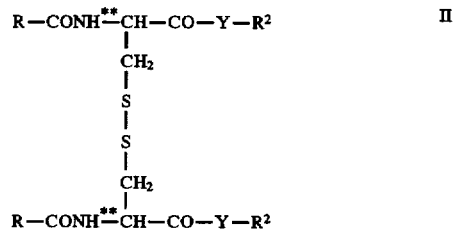

with Zn in an HCl/H$_2$SO$_4$/solvent mixture and reacting with a compound of formula III,

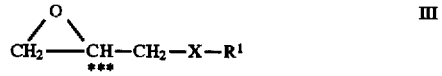

where R, R$^1$ R$^2$, X and Y are as defined above.

2. The process as claimed in claim 1, which is carried out as a one-pot reaction.

* * * * *

UNITED STATES PATENT AND TRADEMARK OFFICE
CERTIFICATE OF CORRECTION

PATENT NO. : 5,700,910
DATED : December 23, 1997
INVENTOR(S) : Jorg METZGER et al.

It is certified that error appears in the above-identified patent and that said Letters Patent is hereby corrected as shown below:

Claim 1, column 8, line 60, after "$R^1$", insert --,--.

Signed and Sealed this

Twenty-first Day of July, 1998

Attest:

BRUCE LEHMAN

*Attesting Officer*  *Commissioner of Patents and Trademarks*